(12) United States Patent
Kumar et al.

(10) Patent No.: US 11,364,082 B2
(45) Date of Patent: Jun. 21, 2022

(54) FUSION-IMAGING METHOD FOR RADIO FREQUENCY ABLATION

(71) Applicant: CHANG BING SHOW CHWAN MEMORIAL HOSPITAL, Changhua County (TW)

(72) Inventors: Atul Kumar, Changhua County (TW); Yen-Yu Wang, Changhua County (TW); Hurng-Sheng Wu, Changhua County (TW); Kai-Che Liu, Changhua County (TW); Shih-Wei Huang, Changhua County (TW); I-Chun Lee, Changhua County (TW); Wan-Chi Hung, Changhua County (TW)

(73) Assignee: CHANG BING SHOW CHWAN MEMORIAL HOSPITAL, Changhua County (TW)

( * ) Notice: Subject to any disclaimer, the term of this patent is extended or adjusted under 35 U.S.C. 154(b) by 211 days.

(21) Appl. No.: 16/655,797

(22) Filed: Oct. 17, 2019

(65) Prior Publication Data
US 2021/0113271 A1 Apr. 22, 2021

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/4254* (2013.01); *A61B 8/5261* (2013.01); *A61B 5/0037* (2013.01);
(Continued)

(58) Field of Classification Search
CPC .......... A61B 18/14; A61B 2018/00529; A61B 2018/00577; A61B 2034/102;
(Continued)

(56) References Cited

U.S. PATENT DOCUMENTS

2011/0137156 A1* 6/2011 Razzaque .......... A61B 18/1477
600/424

OTHER PUBLICATIONS

William E. Lorensen et al. "Marching Cubes: A High Resolution 3D Surface Construction Algorithm" Article in ACM SIGGRAPH Computer Graphics; Aug. 1987; pp. 1-14.
(Continued)

*Primary Examiner* — Michael T Rozanski
(74) *Attorney, Agent, or Firm* — Muncy, Geissler, Olds & Lowe, P.C.

(57) ABSTRACT

A fusion-imaging method for radiofrequency ablation is provided, including: obtaining preoperative volume image of an individual; reconstructing a virtual three-dimensional model of a target area of the individual according to the preoperative volume image; creating a global reference frame by a tracking device and registering the virtual three-dimensional model to the global reference frame; obtaining an ultrasound image of the target area by using an ultrasonic probe and tracking the ultrasonic probe by the tracking device in order to register the ultrasonic image to the global reference frame; capturing a virtual corresponding image corresponding to a portion of the virtual three-dimensional model along a plane of the ultrasonic image; and overlapping the ultrasonic image and the virtual corresponding image and simultaneously displaying the overlapping image and a virtual radiofrequency ablation probe model.

4 Claims, 7 Drawing Sheets

(51) Int. Cl.
*A61B 8/08* (2006.01)
*A61B 34/10* (2016.01)
*A61B 6/03* (2006.01)
*A61B 5/055* (2006.01)
*A61B 5/00* (2006.01)
*A61B 18/00* (2006.01)
*A61B 18/14* (2006.01)
*A61B 90/00* (2016.01)

(52) U.S. Cl.
CPC ............... *A61B 5/055* (2013.01); *A61B 6/032* (2013.01); *A61B 18/14* (2013.01); *A61B 2018/00529* (2013.01); *A61B 2018/00577* (2013.01); *A61B 2034/102* (2016.02); *A61B 2034/105* (2016.02); *A61B 2034/107* (2016.02); *A61B 2034/2063* (2016.02); *A61B 2090/364* (2016.02); *A61B 2090/378* (2016.02)

(58) Field of Classification Search
CPC ........ A61B 2034/105; A61B 2034/107; A61B 2034/2051; A61B 2034/2055; A61B 2034/2063; A61B 2090/364; A61B 2090/378; A61B 34/20; A61B 5/0037; A61B 5/055; A61B 5/061; A61B 6/032; A61B 8/4254; A61B 8/5261
See application file for complete search history.

(56) References Cited

OTHER PUBLICATIONS

D. Chetverikov et al., "The Trimmed Iterative Closest Point algorithm," *Object recognition supported by user interaction for service robots*, Quebec City, Quebec, Canada, 2002, pp. 545-548 vol.3.

* cited by examiner (a) (b)

(a)  (b)

FUSION-IMAGING METHOD FOR RADIO FREQUENCY ABLATION

BACKGROUND OF THE INVENTION

1. Field of the Invention

The present invention relates to a fusion-imaging method, more particularly to a fusion-imaging method for radiofrequency ablation.

2. Description of the Related Art

With the advancement of medical technology, surgery may be operated with the help of various auxiliary instruments to improve the precision in the surgical process, alleviate a burden on surgeons, and enhance the postoperative performance of an individual. Especially, different kinds of surgery may be operated under the guidance of an ultrasound (USG) image. However, due to the low penetrance of the USG image, the deep-seated tumors may not be visible in the USG image.

For instance, several different kinds of liver lesions need to be treated with the help of radiofrequency ablation (RFA). Radiofrequency ablation is done with the help of an RFA probe inserted into the liver under the guidance of the ultrasound (USG) image. Usually, in a USG-guided interventional procedure, the surgeons need to register the reference data set and the real-time working data set of the USG image on their minds, wherein the reference data set is calculated from preoperative volume image such as computed tomography (CT) or magnetic resonance imaging (MRI). This means that surgeons need to imagine a corresponding relation between the preoperative volume image and the real-time image. However, due to the low penetrance of ultrasound, the deep-seated tumors may not be visible in the USG image. In the meantime, this manner may increase the difficulty of surgery and place great burdens on the surgeons Hence, there is still a need for a method that may help the surgeons easily locate deep-seated lesions while providing fusion imaging of real-time images.

SUMMARY OF THE INVENTION

In view of the aforementioned problems, the present invention provides a fusion-imaging method for radiofrequency ablation, including: obtaining preoperative volume image of an individual; reconstructing a virtual three-dimensional model of a target area of the individual according to the preoperative volume image; creating a global reference frame by a tracking device and registering the virtual three-dimensional model to the global reference frame; obtaining an ultrasonic image of the target area by using an ultrasonic probe and tracking the ultrasonic probe by the tracking device in order to register the ultrasonic image to the global reference frame; capturing a virtual corresponding image corresponding to a portion of the virtual three-dimensional model along a plane of the ultrasonic image; and overlapping the ultrasonic image with the virtual corresponding image and simultaneously displaying an overlapping image and a virtual radiofrequency ablation probe model. Wherein the virtual radiofrequency ablation probe model is created by following step: tracking a radiofrequency ablation tracker mounted on a radiofrequency ablation probe by the tracking device to obtain a radiofrequency ablation probe position; reconstructing a virtual model of the radiofrequency ablation probe and the radiofrequency ablation tracker by geometrical parameters of the radiofrequency ablation probe and the radiofrequency ablation tracker to be used as a virtual radiofrequency ablation probe model; and registering the virtual radiofrequency ablation probe model to the global reference frame based on the radiofrequency ablation probe position.

Optionally, the method may further include the following steps: marking at least three marked points of the individual by using the tracking device; selecting the at least three corresponding points corresponding to at least three marked points in the virtual three-dimensional model; and calculating the at least three marked points and the at least three corresponding points by an iterative closest point algorithm in order to register the virtual three-dimensional model to the global reference frame.

Optionally, the step of capturing the virtual corresponding image corresponding to the portion of the virtual three-dimensional model along the plane of the ultrasonic image further include: calculating an edge by intersecting an edge formed by connected points of the virtual three-dimensional model and the plane of the ultrasonic image by using Equation 1;

$$s_I = \frac{n \cdot (V_0 - P_0)}{n \cdot (P_1 - P_0)}; \qquad \text{Equation 1}$$

wherein n is a normal line of the plane of the ultrasonic image, $V_o$ is a point on the plane of the ultrasonic image, and $P_0$ and $P_1$ are the connected points of the virtual three-dimensional model;

If $s_I > 1$, calculating an line passing through the connected points by using Equation 2;

$$t = \frac{x - x_1}{l} = \frac{y - y_1}{m} = \frac{z - z_1}{n}; \qquad \text{Equation 2}$$

wherein x, y, and z are coordinates of a first connected point among the connected points; $x_1$, $y_1$, and $z_1$ are the coordinates of a second connected point among the connected points; l, m, and n are a slope between the first connected point and the second connected point, and t is a variable representing a ratio;

obtaining Equation 3 of the plane of the ultrasonic image;

$$a(x-x_0)+b(y-y_0)+c(z-z_0)=0 \qquad \text{Equation 3;}$$

wherein $x_0$, $y_0$, and $z_0$ are coordinates on the plane of the ultrasonic image, and a, b, and c are normal of the plane of the ultrasonic image calculating a value of t, calculating x, y, and z coordinates by replacing t in Equation 2, and tracking a shortest path of a point pair;

connecting an intersection point by intersecting the edge formed by the connected points of the virtual three-dimensional model and the plane of the ultrasonic image and the point pair to form a closed curve, and interpolating the closed curve to fit a second-degree curve to the virtual corresponding image; and overlapping the ultrasonic image and the virtual corresponding image and displaying the overlapping image and the virtual radiofrequency ablation probe model.

Optionally, the method may further include the following steps: tracking a ultrasonic tracker mounted on the ultrasonic probe by the tracking device to obtain an ultrasonic probe position; reconstructing a virtual model of the ultrasonic probe and the ultrasonic tracker by geometrical parameters of the ultrasonic probe and the ultrasonic tracker to be used as a virtual ultrasonic probe model; registering the virtual ultrasonic probe model to the global reference frame based on the ultrasonic probe position; and overlapping the ultrasonic image and the virtual corresponding image and simultaneously displaying the overlapping image, the virtual radiofrequency ablation probe model and the virtual ultrasonic probe model.

Optionally, the preoperative volume image may obtain from tomography imaging or nuclear magnetic resonance imaging.

The fusion-imaging method for radiofrequency ablation of the present invention has the following advantages:

The present invention provides a fusion-imaging method for the combination of a preoperative 3D virtual model message with a real-time USG image, wherein the fusion-imaging may help the surgeons easily locate deep-seated lesions that are normally not visible in the USG image. Therefore, it is beneficial to locating a lesion in either a superficial or deep-seated position from fusion imaging of the outline of the lesion in the liver calculated from a 3D virtual model reconstructed from preoperative volume images like CT or MRI and the outline of a 3D virtual model of an RFA probe superimposed on the USG image. In so doing, the fusion-imaging method of the present invention may simultaneously provide fusion imaging of preoperative images and real-time images that are accurately calculated and aligned, thus helping the surgeons improve the operational precision during surgery.

In addition, the fusion-imaging method for radiofrequency ablation of the present invention may also simultaneously display the virtual radiofrequency ablation probe model for an RFA probe of radiofrequency ablation (commonly known as the electrocauterization) and the virtual ultrasonic probe model for a USG probe providing the real-time ultrasonic image, enabling the surgeon to clearly distinguish the related position between the probes and the organ when viewing the render window of the display, thus further improving the operational precision during surgery.

DESCRIPTION OF THE PREFERRED EMBODIMENTS

To make the aforementioned purpose, the technical features, and the gains after actual implementation more obvious and understandable to a person of ordinary skill in the art, the following description shall be explained in more detail with reference to the preferable embodiments together with related drawings.

Figure 1:
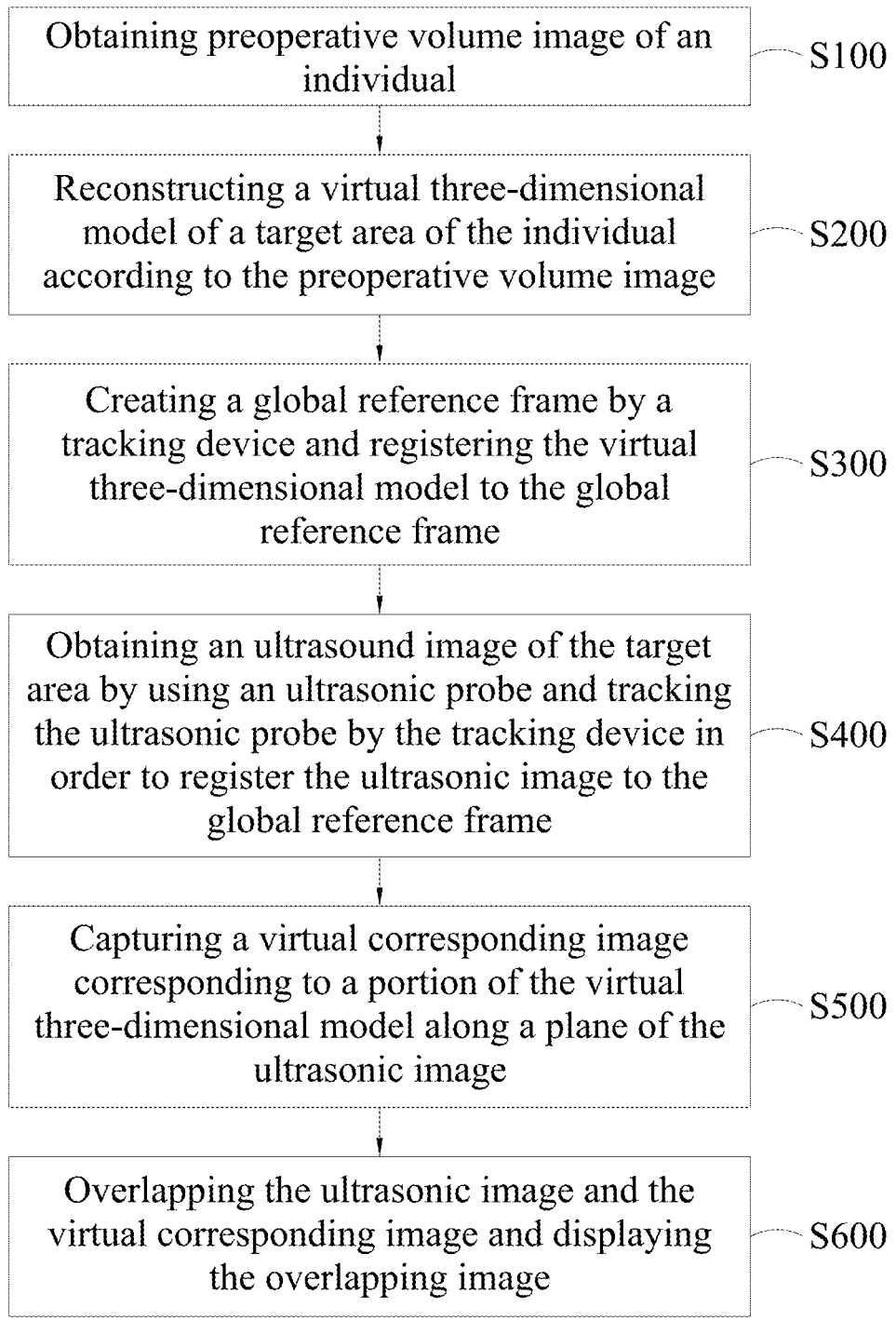
FIG. 1 depicts a flow chart of the fusion-imaging method for radiofrequency ablation according to the present invention.

Please refer to FIG. 1 which depicts a flow chart of the fusion-imaging method for radiofrequency ablation according to the present invention.

In step S100, the preoperative volume image of an individual is obtained. The individual may be a human. The preoperative volume image may be obtained from tomographic imaging, magnetic resonance imaging, or any preoperative volume imaging technique known to a person of ordinary skill in the art.

In step S200, a virtual three-dimensional model of a target area of the individual is reconstructed according to the preoperative volume image of the individual. Wherein, specific organs, tissues, or any combination thereof may be selected according to requirements for the target area, and the target area may include one or more organs, tissues, or any combination thereof. In one embodiment, if the individual suffers from a disease of the liver lesion, the target area may include the liver and the surrounding tissues thereof.

In step S300, a global reference frame is created by a tracking device and the virtual three-dimensional model is registered to the global reference frame. In other words, the virtual coordinates of the virtual three-dimensional model are aligned with the global reference frame constructed by the real tracking device to transform the virtual three-dimensional model into the global reference frame.

In one embodiment, at least three marked points on the individual are marked using the tracking device that constructs the global reference frame. For instance, the marked points may be at the sternal end of the individual's clavicle, the xiphoid, or other organs having obvious positional features such as wrist joints. In the virtual three-dimensional model, at least three corresponding points corresponding to the at least three marked points are manually or automatically selected, wherein the selection method includes clicking using a mouse, inputting commands using a keyboard, and the like. Moreover, the at least three marked points and the at least three corresponding points are calculated by an iterative closest point (ICP) algorithm to register the virtual three-dimensional model which has not been transformed into the global reference frame to the global reference frame so as to allow the subsequent virtual models and the real-time ultrasonic images to be located in the same frame.

In step S400, an ultrasonic image of the target area is obtained by using an ultrasonic probe and the ultrasonic probe is tracked by the tracking device in order to register the ultrasonic image to the global reference frame. In one embodiment, ultrasonic scanning is performed using any suitable conventional ultrasonic probe, and ultrasonic images of the target area of the individual are obtained.

In step S500, a virtual corresponding image corresponding to a portion of the virtual three-dimensional model is captured along the plane of the obtained ultrasonic image. In other words, since the ultrasonic image and virtual three-dimensional model are located in the global reference frame, the virtual corresponding image corresponding to the portion of the virtual three-dimensional model is enabled to be captured along the plane constructed by the ultrasonic image in the virtual three-dimensional model. For example, if the ultrasonic image displays a cross-sectional view of a particular portion of the liver of the individual, a cross-sectional view of the particular portion of the liver of the virtual three-dimensional model of the individual is captured correspondingly.

In step S600, the obtained ultrasonic image and the captured virtual corresponding image are overlapped with each other and the overlapping image is displayed such that the real-time ultrasonic image and the virtual three-dimensional model obtained from preoperative volume image are correspondingly displayed. The overlapping image may be displayed in the render window. The render window may be any display software for a conventional display such as a computer screen.

In an embodiment, in addition to registering the virtual three-dimensional model to the global reference frame to display the virtual three-dimensional model on the render window, it may also be possible to register a virtual radiofrequency ablation probe model, a virtual ultrasonic probe model, a virtual model of other suitable surgical instruments, and any combination thereof.

For example, the ultrasonic tracker mounted on the ultrasonic probe is tracked by the tracking device to obtain the ultrasonic probe position. The virtual model of the ultrasonic probe and the ultrasonic tracker is reconstructed by using the real geometrical parameters of the ultrasonic probe and the ultrasonic tracker to be used as a virtual ultrasonic probe model, wherein the real geometrical parameters may be the length, width, height, and other specific parameters of sizes. Since the tracking device constructs the global reference frame, the virtual ultrasonic probe model is registered to the global reference frame based on the ultrasonic probe position. Moreover, the ultrasonic image and the virtual corresponding image are overlapped with each other, and the overlapping image and the virtual ultrasonic probe model are displayed to enable the surgeon to simultaneously view the related position of the overlapping image and the virtual ultrasonic probe model in the render window.

Similarly, the radiofrequency ablation tracker mounted on the radiofrequency ablation probe may also be tracked by the tracking device to obtain the radiofrequency ablation probe position. The virtual model of the radiofrequency ablation probe and the radiofrequency ablation tracker is reconstructed by using the real geometrical parameters of the radiofrequency ablation probe and the radiofrequency ablation tracker to be used as a virtual radiofrequency ablation probe model, wherein the real geometrical parameters may be the length, width, height, and other specific parameters of sizes. The virtual radiofrequency ablation probe model is registered to the global reference frame based on the radiofrequency ablation probe position. The ultrasonic image and the virtual corresponding image are overlapped with each other, and the related position of the overlapping image and the virtual radiofrequency ablation probe model is simultaneously displayed.

In short, the fusion-imaging method for radiofrequency ablation according to the present invention may achieve the purpose of simultaneously displaying inspection results of preoperative precision instrument and real-time images by introducing preoperative images and real-time images into the same frame, thus improving the precision of surgery.

Hereafter, the fusion-imaging method for radiofrequency ablation of the present invention is further described by specific examples.

Figure 2:
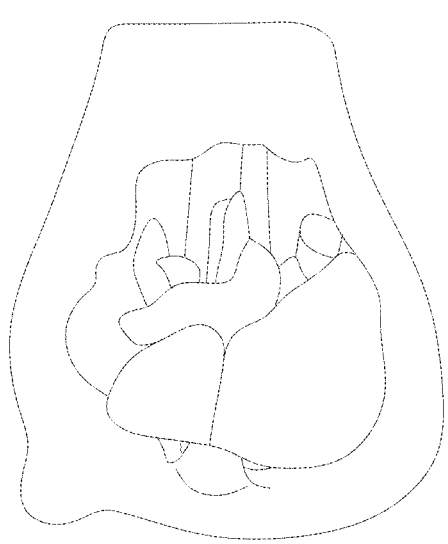
FIG. 2 depicts a schematic diagram of the target area and the virtual three-dimensional model of the fusion-imaging method for radiofrequency ablation according to the present invention.
Figure 2:
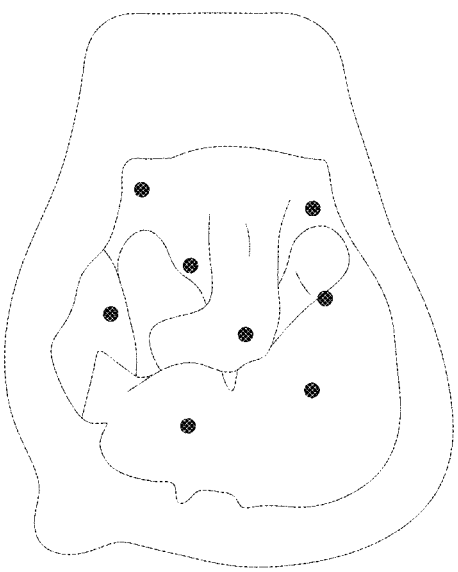

Please refer to FIG. 2 which depicts a schematic diagram of the fusion-imaging method for radiofrequency ablation according to the present invention, wherein (a) is a schematic diagram of the target area, and (b) is a schematic diagram of the virtual three-dimensional model.

The Virtual Three-Dimensional Model of the Organ:

The image of the preoperative volume image such as CT scanning image or MRI image is segmented, and the segmented image is selected by a user as the target area. A 3D virtual model of the organ is reconstructed using the volume reconstruction algorithm (referring to: Lorensen, William E., and Harvey E. Cline. "Marching cubes: A high resolution 3D surface construction algorithm." ACM siggraph computer graphics. Vol. 21. No. 4. ACM, 1987.). Wherein, the target area may be a peritoneal cavity of a human body. In addition, the points shown in FIG. 2 may respectively be marked points and corresponding points.

Figure 3:
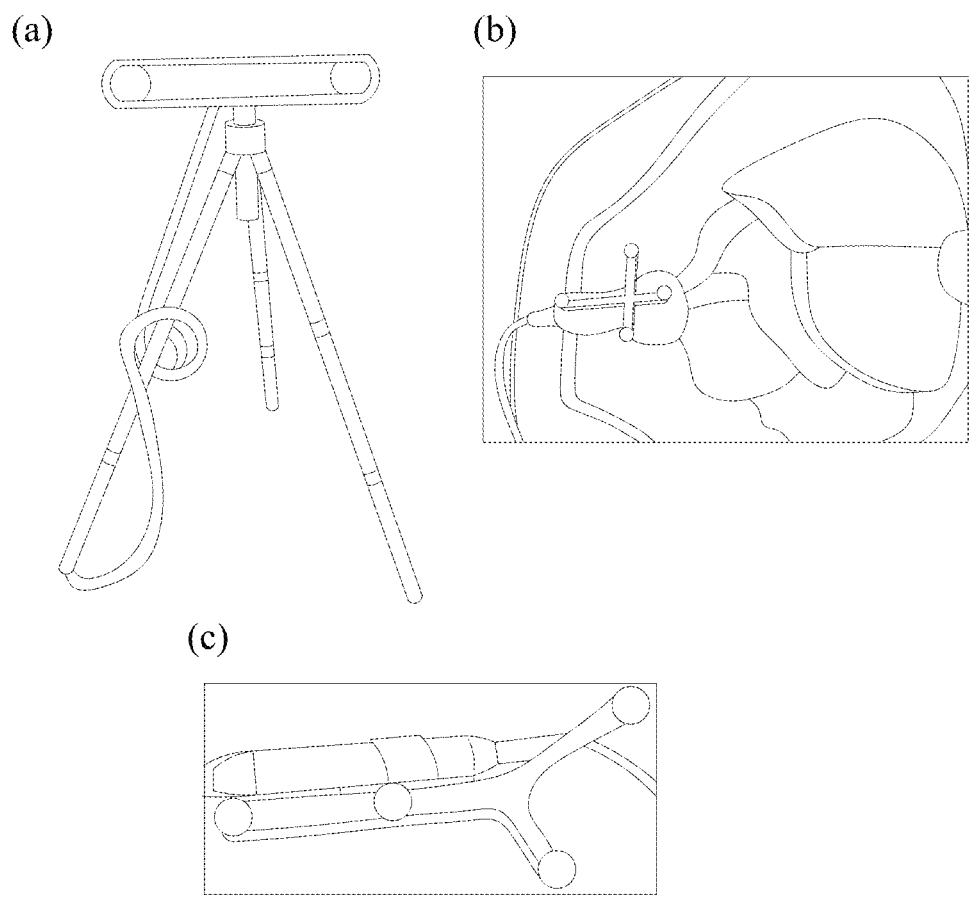
FIG. 3 depicts a tracking device diagram of the fusion-imaging method for radiofrequency ablation according to the present invention.

Please refer to FIG. 3 which depicts a schematic diagram of the fusion-imaging method for radiofrequency ablation according to the present invention, wherein (a) is a schematic diagram of the tracking device, (b) is a schematic diagram of the ultrasonic probe mounted with the tracker, (c) is a schematic diagram of the radiofrequency ablation probe mounted with the tracker.

The Tracking System:

A position tracking system based on an infrared tracking principle or an electromagnetic field is used to track the USG probe and the RFA probe. The trackers of the tracking device are respectively mounted on the USG probe and the RFA probe. The tracking device may be used as the position tracking system, and the reference frame may be considered to be the global reference frame of the fusion-imaging method for radiofrequency ablation of the present invention.

The Visualization Software:

Any conventional visualization software may be used to make the virtual three-dimensional model display on the display. The software interface provides a visualization of a virtual model of the organ ($Organ_{Model}$), the USG probe ($USG_{Model}$) and the RFA probe ($RFA_{Model}$) along with the real-time USG image ($USG_{Image}$) in a render window of the virtual environment.

Registration and Updating Positions:

Registration of the body of the individual to the global reference frame: A registration technique with manually and/or automatically marking selections is used to register the 3D organ model to the global reference frame.

Figure 4:
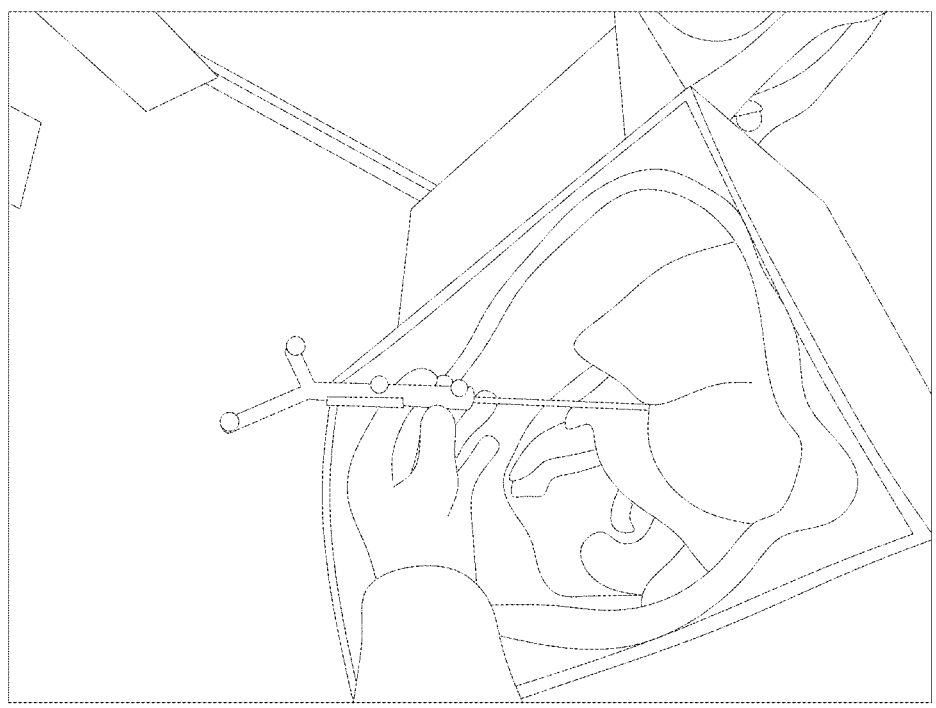
FIG. 4 depicts a schematic diagram of the marking method of the fusion-imaging method for radiofrequency ablation according to the present invention.

Please refer to FIG. 4 depicts a schematic diagram of the marked points of the fusion-imaging method for radiofrequency ablation of the present invention.

After the setup of the system, the virtual three-dimensional model is rendered in the render window of the graphical user interface (GUI) of the software. Please refer to FIG. 4 together with FIG. 2. The at least three or more marked points of the individual are recorded by using a position sensing tool. That position sensing tool is the tracking device, the tracker mounted on the ultrasonic probe, or the tracker mounted on the radiofrequency ablation probe. In the individual, the at least three or more marked points such as the sternal end of the clavicles and xiphoid process, may be selected for the registration.

Figure 5:
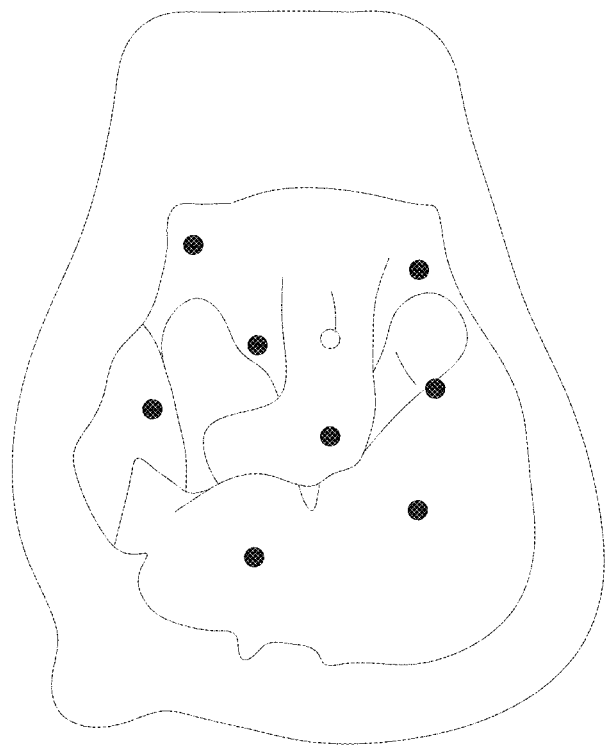
FIG. 5 depicts a schematic diagram of the corresponding points of the fusion-imaging method for radiofrequency ablation according to the present invention.

Please refer to FIG. 5 which depicts a schematic diagram of the corresponding points of the fusion-imaging method for radiofrequency ablation of the present invention. A mouse is used to click on the corresponding points of the virtual model of the individual displayed on the render window.

Figure 6:
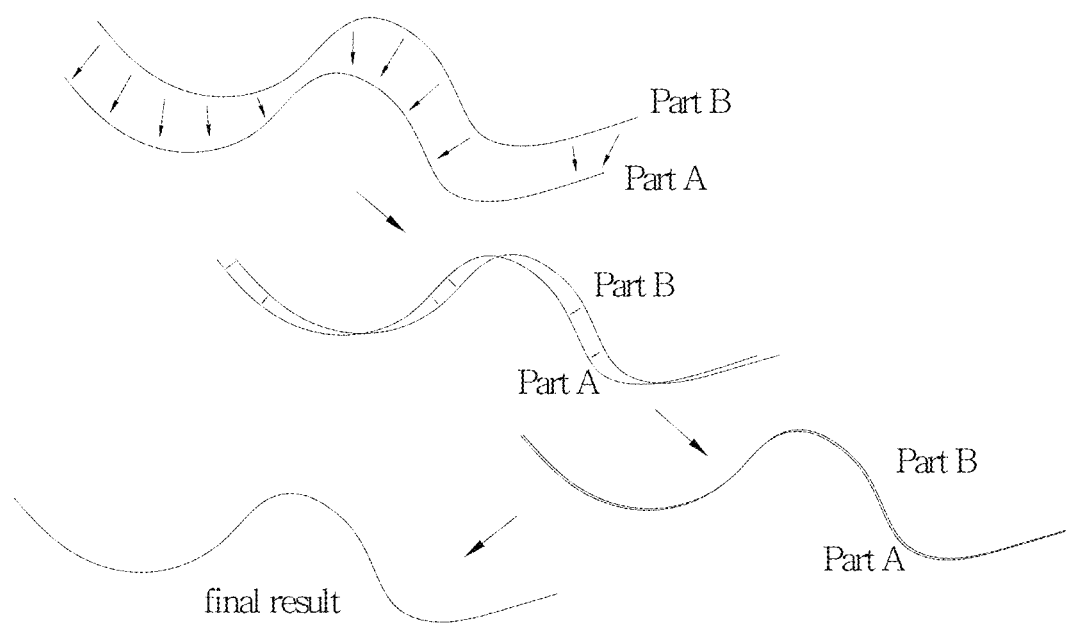
FIG. 6 depicts a schematic diagram of the iterative closest point algorithm of the fusion-imaging method for radiofrequency ablation according to the present invention.

Please refer to FIG. 6. With the use of the corresponding points, an iterative closest point algorithm (ICP) (referring to: Chetverikov, Dmitry, et al. "The trimmed iterative closest point algorithm." Object recognition supported by user interaction for service robots. Vol. 3. IEEE, 2002) is applied to calculate a transformation matrix. As shown in FIG. 6, with the use of the ICP algorithm, the line segment of part A and the line segment of part B are calculated so as to visualize the registration. Particularly, the transformation matrix in the process of the ICP algorithm is applied to the entire virtual three-dimensional model of the organ to introduce the virtual three-dimensional model into the global reference frame.

USG Probe Model to the Global Reference Frame:

The ultrasonic tracker is fixed on the USG probe. Since the geometrical parameters used to design the USG probe and the ultrasonic tracker are known, that is, the specific sizes of the geometry (length, width, height) of the USG probe and the ultrasonic tracker are known, the position of the USG probe where the ultrasonic tracker is mounted on is known such that the related position between the ultrasonic tracker and the USG probe is also known. Based on the geometry of the USG probe and the ultrasonic tracker, the assembled virtual three-dimensional model is reconstructed as a virtual ultrasonic probe model which is then displayed on the render window.

The information on the size of the USG image (unit: mm) is obtained from the USG manufacturer's manual. A bounding box to a head of the probe is calculated. An image plane perpendicular to the distal surface of the bounding box is drawn and the physical size (in millimeters or centimeters) of the USG image is created in the render window of the virtual environment. The plane is filled with the pixel intensity of the USG image. An tip of the USG probe may be found from the distal surface of the bounding box that is tangent to the distal surface of the USG probe model.

Figure 7:
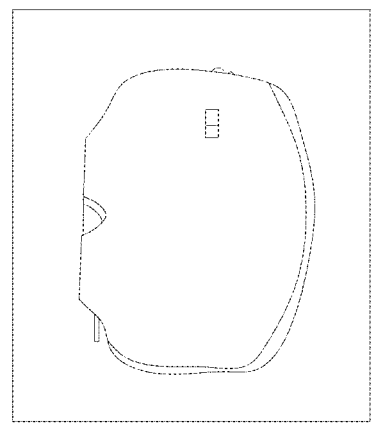
FIG. 7 depicts a schematic diagram of the image transformation of the fusion-imaging method for radiofrequency ablation according to the present invention.
Figure 7:
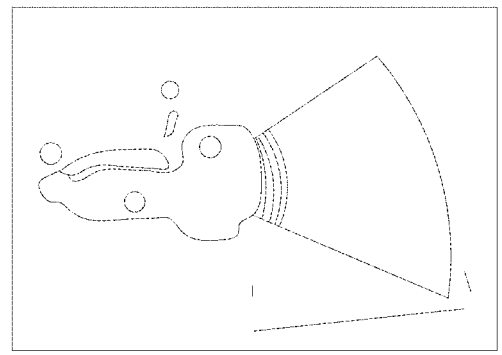

Please refer to FIG. 7 which depicts a schematic diagram of the image transformation of the fusion-imaging method for radiofrequency ablation according to the present invention. The image plane is further transformed to this point so that the center of the proximal curvature in the image passes through the tip of the USG probe. Since the local reference frame of the ultrasonic tracker is known from the manufacturer's manual, the complete assembly is placed in the render window such that the local reference frame is aligned with the global reference frame of the render window. The position of the virtual model of the ultrasonic tracker is then updated by the transformation obtained by the current position of the real ultrasonic tracker. The same transformation is applied to the complete assembly.

Registration of the Radiofrequency Probe Model:

The radiofrequency ablation tracker is mounted to the radiofrequency ablation probe to make it suitable for any radiofrequency probe at the groove on the proximal end thereof. Similarly, a virtual radiofrequency ablation probe model of the RFA probe with the mounted radiofrequency ablation tracker is reconstructed based on the geometrical parameters of the radiofrequency ablation tracker and the radiofrequency ablation probe. Since the local reference frame of the radiofrequency ablation tracker is known, the virtual model of the radiofrequency ablation tracker is moved by the transformation recorded from the current position of the radiofrequency ablation tracker. The same transformation is used to move the complete assembly of the virtual model of the RFA probe with the mounted radiofrequency ablation tracker.

Display of the Area of USG and the Virtual Model:

The virtual model of the organ is in the form of the STL file which constitutes connected points in the three-dimensional model. The connection between the connected points is called "edges". All the edges intersected by the image plane are found using the equations of the line segment and plane intersection equation (Equation 1).

$$s_I = \frac{n \cdot (V_0 - P_0)}{n \cdot (P_1 - P_0)} \quad \text{(Equation 1)}$$

Wherein, n is a normal line of the plane, $V_o$ is a point on the plane, and $P_0$ and $P_1$ are the points of the line segment. If $s_I > 1$, the plane is intersected by the edge (line segment). Once the edge intersecting the plane is known, the equation of the line passing through the two points of the line segment may be found using the virtual-dimensional coordinates of the points and the slope (Equation 2).

$$t = \frac{x - x_1}{l} = \frac{y - y_1}{m} = \frac{z - z_1}{n} \quad \text{(Equation 2)}$$

Wherein, x, y, and z are the coordinates of one of the points; $x_1$, $y_1$, and $z_1$ are the coordinates of another one of the points; l, m, and n are the slopes between the points, and t is a variable representing a ratio. The equation of the plane is found using a point on the plane and the normal line passing through the point (Equation 3).

$$a(x-x_0)+b(y-y_0)+c(z-z_0)=0 \quad \text{(Equation 3)}$$

Wherein, $x_0$, $y_0$, and $z_0$ are the coordinates of the point on the plane; a, b, and c are the normal lines of the plane passing through the point. The value of t is calculated using Equation 2 and Equation 3. Then, x, y, and z coordinates are calculated by replacing t in Equation 2. Hence, the intersection points of the plane and the edges are calculated.

Figure 8:
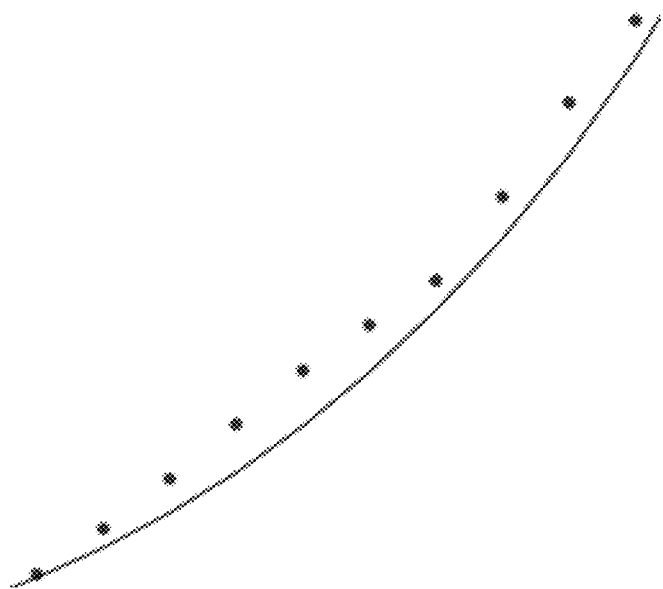
FIG. 8 and FIG. 9 depict schematic diagrams of the interpolation method of the fusion-imaging method for radiofrequency ablation according to the present invention.
Figure 9:
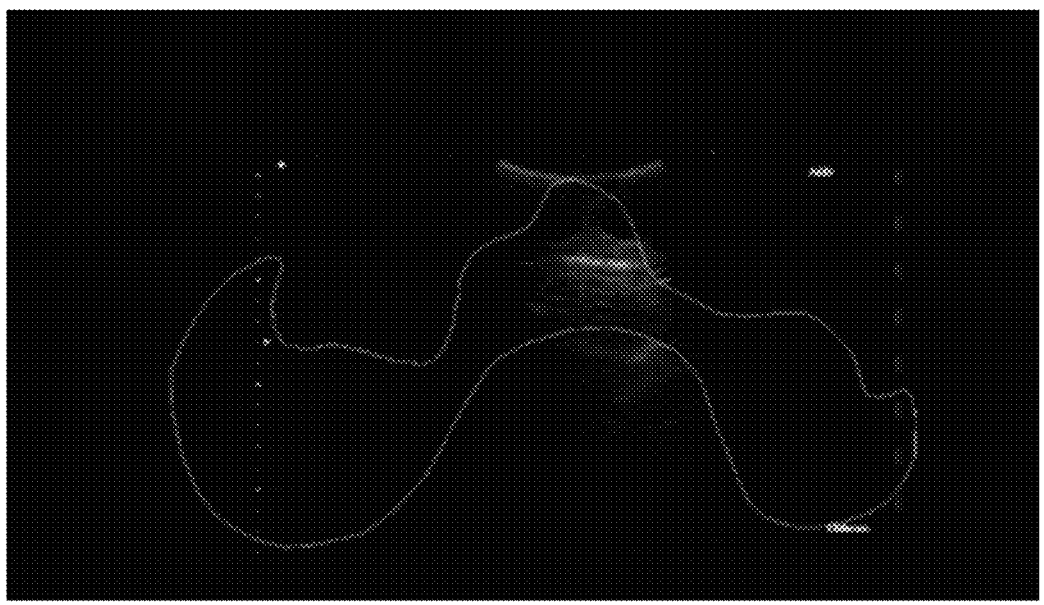

Please refer to FIG. 8 and FIG. 9 which depict schematic diagrams of the interpolation method of the fusion-imaging method for radiofrequency ablation according to the present invention. The shortest path between each point pair is traced and the point pairs are connected to form a closed space by the intersection points between edges and the plane. The paths are interpolated to generate more points between point pairs using a second-degree curve fitting to the multiple adjacent points (on either side). The connected paths are overlapped and displayed on the ultrasonic image.

Figure 10:
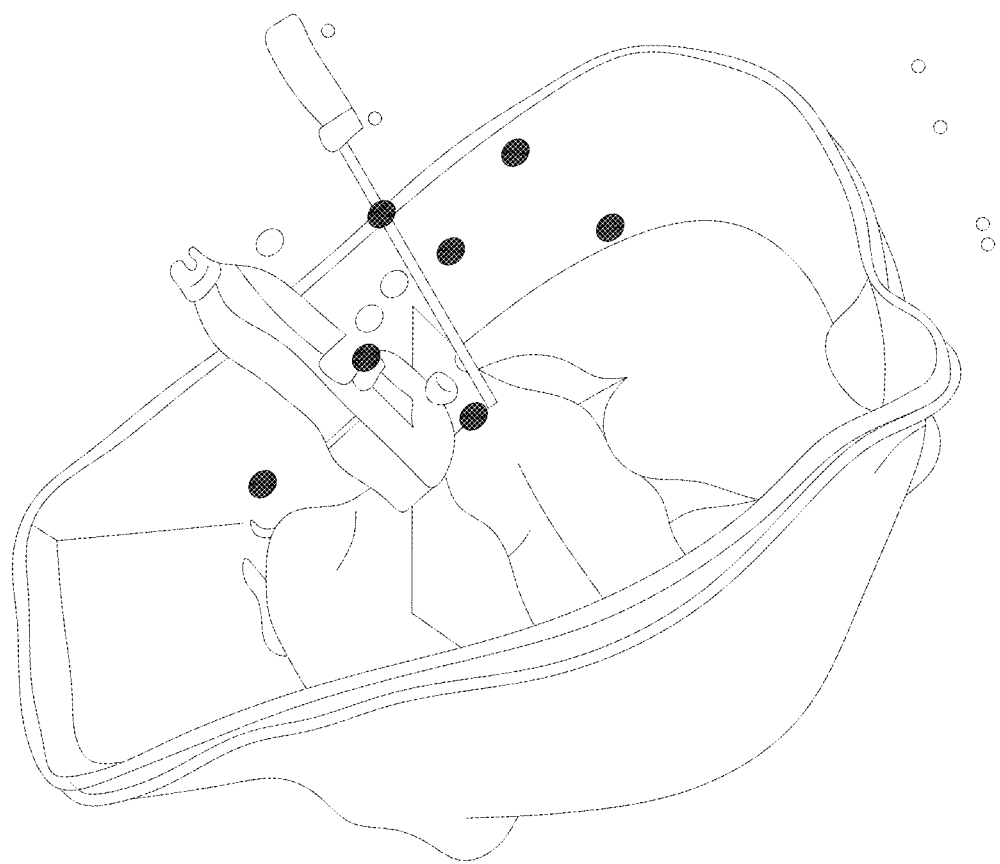
FIG. 10 depicts a schematic diagram of the render window of the fusion-imaging method for radiofrequency ablation according to the present invention.

Please refer to FIG. 10 which depicts a schematic diagram of the render window of the fusion-imaging method for radiofrequency ablation according to the present invention. In a separate render window, the virtual three-dimensional model of the organ, the ultrasonic image, the virtual ultrasonic probe model, and the virtual radiofrequency ablation probe model are displayed together in the render window.

The present invention has specifically described the fusion-imaging method for radiofrequency ablation in the aforementioned embodiment. However, it is to be understood by a person of ordinary skill in the art that modifications and variations of the embodiment may be made without departing from the spirit and scope of the present invention. Therefore, the scope of the present invention shall be described as in the following claims.

What is claimed is:

1. A fusion-imaging method for radiofrequency ablation, comprising:
   obtaining a preoperative volume image of an individual;
   reconstructing a virtual three-dimensional model of a target area of the individual according to the preoperative volume image;
   creating a global reference frame by a tracking device and registering the virtual three-dimensional model to the global reference frame;
   obtaining an ultrasonic image of the target area by using an ultrasonic probe and tracking the ultrasonic probe by the tracking device in order to register the ultrasonic image to the global reference frame;
   capturing a virtual corresponding image corresponding to a portion of the virtual three-dimensional model along a plane of the ultrasonic image; and
   overlapping the ultrasonic image with the virtual corresponding image and simultaneously displaying an overlapping image and a virtual radiofrequency ablation probe model, wherein the virtual radiofrequency ablation probe model is created by following steps:
   tracking a radiofrequency ablation tracker mounted on a radiofrequency ablation probe by the tracking device to obtain a radiofrequency ablation probe position;
   reconstructing a virtual model of the radiofrequency ablation probe and the radiofrequency ablation tracker by geometrical parameters of the radiofrequency ablation probe and the radiofrequency ablation tracker to be used as the virtual radiofrequency ablation probe model; and
   registering the virtual radiofrequency ablation probe model to the global reference frame based on the radiofrequency ablation probe positions;
   wherein the step of capturing the virtual corresponding image corresponding to the portion of the virtual three-dimensional model along the plane of the ultrasonic image further comprises:
   calculating an edge by intersecting an edge formed by connected points of the virtual three-dimensional model and the plane of the ultrasonic image by using Equation 1;

$$s_I = \frac{n \cdot (V_0 - P_0)}{n \cdot (P_1 - P_0)};$$ Equation 1 wherein n is a normal line of the plane of the ultrasonic image, $V_o$ is a point on the plane of the ultrasonic image, and $P_0$ and $P_1$ are the connected points of the virtual three-dimensional model;
   if $s_I>1$, calculating a line passing through the connected points by using Equation 2;

$$t = \frac{x - x_1}{l} = \frac{y - y_1}{m} = \frac{z - z_1}{n};$$ Equation 2 wherein x, y, and z are coordinates of a first connected point among the connected points; $x_1$, $y_1$, and $z_1$ are the coordinates of a second connected point among the connected points; l, m, and n are slopes between the first connected point and the second connected point, and t is a variable representing a ratio;
   obtaining Equation 3 of the plane of the ultrasonic image;

$$a(x-x_0)+b(y-y_0)+c(z-z_0)=0$$ Equation 3;

wherein $x_0$, $y_0$, and $z_0$ are coordinates on the plane of the ultrasonic image, and a, b, and c are normal of the plane of the ultrasonic image;
   calculating a value of t, calculating the x, y, and z coordinates by replacing t in Equation 2, and tracking a shortest path of a point pair;
   connecting an intersection point by intersecting the edge formed by the connected points of the virtual three-dimensional model and the plane of the ultrasonic image and the point pair to form a closed curve, and interpolating the closed curve to fit a second-degree curve to the virtual corresponding image; and
   overlapping the ultrasonic image and the virtual corresponding image and displaying the overlapping image and the virtual radiofrequency ablation probe model.

2. The method according to claim 1, further comprising following steps:
   marking at least three marked points of the individual by using the tracking device;
   selecting at least three corresponding points corresponding to the at least three marked points in the virtual three-dimensional model; and
   calculating the at least three marked points and the at least three corresponding points by an iterative closest point algorithm in order to register the virtual three-dimensional model to the global reference frame.

3. The method according to claim 1, further comprising the following steps:
   tracking an ultrasonic tracker mounted on the ultrasonic probe by the tracking device to obtain an ultrasonic probe position;
   reconstructing a virtual model of the ultrasonic probe and the ultrasonic tracker by geometrical parameters of the ultrasonic probe and the ultrasonic tracker to be used as a virtual ultrasonic probe model;
   registering the virtual ultrasonic probe model to the global reference frame based on the ultrasonic probe position; and
   overlapping the ultrasonic image and the virtual corresponding image and simultaneously displaying the overlapping image, the virtual radiofrequency ablation probe model and the virtual ultrasonic probe model.

4. The method according to claim 1, wherein the preoperative volume image is obtained from tomography imaging or nuclear magnetic resonance imaging.

* * * * *